US010226208B2

(12) United States Patent
Emery et al.

(10) Patent No.: US 10,226,208 B2
(45) Date of Patent: *Mar. 12, 2019

(54) ANALYTE DETECTION DEVICES AND METHODS WITH HEMATOCRIT/VOLUME CORRECTION AND FEEDBACK CONTROL

(71) Applicant: Intuity Medical, Inc., Sunnyvale, CA (US)

(72) Inventors: Jeffrey L. Emery, Redwood City, CA (US); Carole R. Stivers, Palo Alto, CA (US)

(73) Assignee: Intuity Medical, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/177,041

(22) Filed: Jun. 8, 2016

(65) Prior Publication Data

US 2017/0095188 A1 Apr. 6, 2017

Related U.S. Application Data

(63) Continuation of application No. 14/614,177, filed on Feb. 4, 2015, now Pat. No. 9,366,636, which is a (Continued)

(51) Int. Cl.
| | |
|---|---|
| *A61B 5/157* | (2006.01) |
| *G01N 33/52* | (2006.01) |
| *G01N 33/66* | (2006.01) |
| *A61B 5/145* | (2006.01) |
| *A61B 5/1455* | (2006.01) |
| *A61B 5/00* | (2006.01) |
| *A61B 5/155* | (2006.01) |

(Continued)

(52) U.S. Cl.
CPC ............ *A61B 5/157* (2013.01); *A61B 5/1455* (2013.01); *A61B 5/1495* (2013.01);
(Continued)

(58) Field of Classification Search
CPC ............ A61B 5/14532; A61B 5/14535; A61B 5/14546; A61B 5/681; A61B 2562/0295;
(Continued)

(56) References Cited

U.S. PATENT DOCUMENTS

| 842,690 A | 1/1907 | Oswalt |
|---|---|---|
| D137,874 S | 5/1944 | Partridge |

(Continued)

FOREIGN PATENT DOCUMENTS

| CA | 2 513 465 A1 | 8/2004 |
|---|---|---|
| DE | 199 22 413 A1 | 11/2000 |

(Continued)

OTHER PUBLICATIONS

ADA Consensus Development Panel. (Jan.-Feb. 1987). "Consensus Statement on Self-Monitoring of Blood Glucose," *Diabetes Care* 10(1):95-99.

(Continued)

*Primary Examiner* — Rebecca M Fritchman
(74) *Attorney, Agent, or Firm* — Cooley LLP

(57) ABSTRACT

Disclosed are devices, arrangements and methods for quantifying the concentration of an analyte present in bodily fluid, including: an assay pad having at least one chemical reagent capable of producing a detectable signal in the form of a reaction spot upon reaction with the analyte; a light source; a detector array; a processor; and a memory in communication with the processor, the memory comprising: (a) at least one value indicative of one or more of: (i) the level of hematocrit contained in the sample; (ii) the volume of the sample applied to the assay pad; or (iii) imperfections present in the reaction spot; and (b) at least one algorithm for calculating the concentration of the analyte contained in the sample.

28 Claims, 4 Drawing Sheets

Related U.S. Application Data continuation of application No. 13/037,089, filed on Feb. 28, 2011, now Pat. No. 8,969,097, which is a continuation of application No. 11/239,122, filed on Sep. 30, 2005, now abandoned.

(60) Provisional application No. 60/689,546, filed on Jun. 13, 2005.

(51) Int. Cl.
*A61B 5/15* (2006.01)
*A61B 5/1495* (2006.01)
*G01N 21/78* (2006.01)

(52) U.S. Cl.
CPC .......... *A61B 5/14532* (2013.01); *A61B 5/155* (2013.01); *A61B 5/150358* (2013.01); *A61B 5/6831* (2013.01); *G01N 21/78* (2013.01); *G01N 33/523* (2013.01); *G01N 33/66* (2013.01); *A61B 2562/0295* (2013.01)

(58) Field of Classification Search
CPC ............. A61B 5/155; G01N 33/54373; G01N 2021/752; Y10S 435/895
USPC .......................................... 600/583; 422/420
See application file for complete search history.

(56) References Cited

U.S. PATENT DOCUMENTS

| | | |
|---|---|---|
| 2,749,797 A | 3/1950 | Harks |
| 3,092,465 A | 6/1963 | Adams, Jr. |
| 3,310,002 A | 3/1967 | Wilburn |
| 3,620,209 A | 11/1971 | Kravitz |
| 3,623,475 A | 11/1971 | Sanz et al. |
| 3,626,929 A | 12/1971 | Sanz et al. |
| 3,630,957 A | 12/1971 | Rey |
| D223,165 S | 3/1972 | Komendat |
| 3,723,064 A | 3/1973 | Liotta |
| 3,741,197 A | 6/1973 | Sanz et al. |
| 3,961,898 A | 6/1976 | Neeley et al. |
| 4,014,328 A | 3/1977 | Cluff et al. |
| 4,042,335 A | 8/1977 | Clement |
| 4,057,394 A | 11/1977 | Genshaw |
| 4,109,655 A | 8/1978 | Chacomac |
| 4,250,257 A | 2/1981 | Lee et al. |
| 4,254,083 A | 3/1981 | Columbus |
| 4,258,001 A | 3/1981 | Pierce et al. |
| 4,260,257 A | 4/1981 | Neeley et al. |
| 4,289,459 A | 9/1981 | Neeley et al. |
| 4,321,397 A | 3/1982 | Nix et al. |
| 4,350,762 A | 9/1982 | DeLuca et al. |
| 4,394,512 A | 7/1983 | Batz |
| 4,414,975 A | 11/1983 | Ryder et al. |
| 4,416,279 A | 11/1983 | Lindner et al. |
| 4,418,037 A | 11/1983 | Katsuyama et al. |
| 4,422,941 A | 12/1983 | Vaughan, Jr. et al. |
| 4,429,700 A | 2/1984 | Thees et al. |
| 4,627,445 A | 12/1986 | Garcia et al. |
| 4,637,403 A | 1/1987 | Garcia et al. |
| 4,637,406 A | 1/1987 | Guinn et al. |
| 4,653,513 A | 3/1987 | Dombrowski |
| 4,661,319 A | 4/1987 | Lape |
| 4,702,261 A | 10/1987 | Cornell et al. |
| 4,711,250 A | 12/1987 | Gilbaugh, Jr. et al. |
| 4,737,458 A | 4/1988 | Batz et al. |
| 4,767,415 A | 8/1988 | Duffy |
| 4,774,192 A | 9/1988 | Terminiello et al. |
| 4,790,979 A | 12/1988 | Terminiello et al. |
| 4,794,926 A | 1/1989 | Munsch et al. |
| 4,815,843 A | 3/1989 | Tiefenthaler et al. |
| 4,829,470 A | 5/1989 | Wang |
| 4,846,785 A | 7/1989 | Cassou et al. |
| 4,887,306 A | 12/1989 | Hwang et al. |
| 4,920,977 A | 5/1990 | Haynes |
| 4,929,426 A | 5/1990 | Bodai et al. |
| 4,930,525 A | 6/1990 | Palestrant |
| 4,935,346 A | 6/1990 | Phillips |
| 4,953,552 A | 9/1990 | De Marzo |
| 4,966,646 A | 10/1990 | Zdeblick |
| 4,995,402 A | 2/1991 | Smith |
| 5,029,583 A | 7/1991 | Meserol |
| 5,049,487 A | 9/1991 | Phillips et al. |
| 5,050,617 A | 9/1991 | Columbus et al. |
| 5,059,394 A | 10/1991 | Phillips et al. |
| 5,077,199 A | 12/1991 | Basagni et al. |
| 5,094,943 A | 3/1992 | Siedel et al. |
| 5,110,724 A | 5/1992 | Hewett |
| 5,114,350 A | 5/1992 | Hewett |
| 5,116,759 A | 5/1992 | Klainer et al. |
| 5,131,404 A | 7/1992 | Neeley et al. |
| 5,141,868 A | 8/1992 | Shanks et al. |
| 5,145,565 A | 9/1992 | Kater et al. |
| 5,146,437 A | 9/1992 | Boucheron |
| 5,153,416 A | 10/1992 | Neeley |
| 5,164,575 A | 11/1992 | Neeley et al. |
| 5,166,498 A | 11/1992 | Neeley |
| 5,174,291 A | 12/1992 | Schoonen et al. |
| 5,176,632 A | 1/1993 | Bernardi |
| 5,179,005 A | 1/1993 | Phillips et al. |
| 5,183,741 A | 2/1993 | Arai et al. |
| 5,196,302 A | 3/1993 | Kidwell |
| 5,208,163 A | 5/1993 | Charlton et al. |
| 5,213,966 A | 5/1993 | Vuorinen et al. |
| 5,217,480 A | 6/1993 | Habar et al. |
| 5,218,966 A | 6/1993 | Yamasawa |
| 5,223,219 A | 6/1993 | Subramanian et al. |
| 5,228,972 A | 7/1993 | Osaka et al. |
| 5,234,818 A | 8/1993 | Zimmermann et al. |
| 5,241,969 A | 9/1993 | Carson et al. |
| 5,251,126 A | 10/1993 | Kahn et al. |
| D341,848 S | 11/1993 | Bigelow et al. |
| 5,275,159 A | 1/1994 | Griebel |
| 5,278,079 A | 1/1994 | Gubinski et al. |
| 5,288,646 A | 2/1994 | Lundsgaard et al. |
| 5,299,571 A | 4/1994 | Mastrototaro |
| 5,301,686 A | 4/1994 | Newman |
| 5,302,513 A | 4/1994 | Mike et al. |
| 5,304,468 A | 4/1994 | Phillips et al. |
| 5,306,623 A | 4/1994 | Kiser et al. |
| 5,308,767 A | 5/1994 | Terashima |
| 5,320,607 A | 6/1994 | Ishibashi |
| 5,354,537 A | 10/1994 | Moreno |
| 5,360,595 A | 11/1994 | Bell et al. |
| 5,368,047 A | 11/1994 | Suzuki et al. |
| 5,383,512 A | 1/1995 | Jarvis |
| 5,390,671 A | 2/1995 | Lord et al. |
| 5,399,316 A | 3/1995 | Yamada |
| 5,401,110 A | 3/1995 | Neeley |
| 5,402,798 A | 4/1995 | Swierczek et al. |
| 5,426,032 A | 6/1995 | Phillips et al. |
| 5,441,513 A | 8/1995 | Roth |
| 5,451,350 A | 9/1995 | Macho et al. |
| 5,458,140 A | 10/1995 | Eppstein et al. |
| 5,460,777 A | 10/1995 | Kitajima et al. |
| 5,460,968 A | 10/1995 | Yoshida et al. |
| 5,482,473 A | 1/1996 | Lord et al. |
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,527,892 A | 6/1996 | Borsotti et al. |
| 5,563,042 A | 10/1996 | Phillips et al. |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |
| 5,611,809 A | 3/1997 | Marshall et al. |
| 5,624,458 A | 4/1997 | Lipscher |
| 5,630,986 A | 5/1997 | Charlton et al. |

(56) References Cited

U.S. PATENT DOCUMENTS

| | | |
|---|---|---|
| 5,632,410 A | 5/1997 | Moulton et al. |
| 5,636,632 A | 6/1997 | Bommannan et al. |
| 5,647,851 A | 7/1997 | Pokras |
| 5,658,515 A | 8/1997 | Lee et al. |
| 5,660,791 A | 8/1997 | Brenneman et al. |
| 5,670,031 A | 9/1997 | Hintsche et al. |
| 5,676,850 A | 10/1997 | Reed et al. |
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,701,181 A | 12/1997 | Boiarski et al. |
| 5,701,910 A | 12/1997 | Powles et al. |
| 5,705,018 A | 1/1998 | Hartley |
| 5,708,247 A | 1/1998 | McAleer |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,797,693 A | 8/1998 | Jaeger |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,854,074 A | 12/1998 | Charlton et al. |
| D403,975 S | 1/1999 | Douglas et al. |
| 5,855,801 A | 1/1999 | Lin et al. |
| 5,856,195 A | 1/1999 | Charlton et al. |
| 5,858,194 A | 1/1999 | Bell |
| 5,866,281 A | 2/1999 | Guckel et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,885,839 A | 3/1999 | Lingane et al. |
| 5,891,053 A | 4/1999 | Sesekura |
| 5,893,870 A | 4/1999 | Talen et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,175,752 B1 | 1/2001 | Say et al. |
| 6,176,865 B1 | 1/2001 | Mauze et al. |
| 6,183,434 B1 | 2/2001 | Eppstein et al. |
| 6,183,489 B1 | 2/2001 | Douglas et al. |
| 6,187,210 B1 | 2/2001 | Lebouiz et al. |
| 6,192,891 B1 | 2/2001 | Gravel et al. |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,888 B1 | 11/2001 | Wong et al. |
| 6,322,808 B1 | 11/2001 | Trautman et al. |
| 6,329,161 B1 | 12/2001 | Heller et al. |
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |

(56) References Cited

U.S. PATENT DOCUMENTS

| | | |
|---|---|---|
| 6,375,627 B1 | 4/2002 | Mauze et al. |
| 6,379,969 B1 | 4/2002 | Mauze et al. |
| 6,391,005 B1 | 5/2002 | Lum et al. |
| 6,391,645 B1 | 5/2002 | Huang et al. |
| 6,409,679 B2 | 6/2002 | Pyo |
| 6,428,664 B1 | 8/2002 | BhulLar et al. |
| 6,449,608 B1 | 9/2002 | Morita et al. |
| 6,455,324 B1 | 9/2002 | Douglas |
| 6,493,069 B1 | 12/2002 | Nagashimada et al. |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,475 B1 | 4/2003 | Douglas et al. |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,707,554 B1 | 3/2004 | Miltner et al. |
| 6,740,800 B1 | 5/2004 | Cunningham |
| 6,748,275 B2 | 6/2004 | Lattner et al. |
| 6,753,187 B2 | 6/2004 | Cizdziel et al. |
| 6,766,817 B2 | 7/2004 | da Silva |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,156,809 B2 | 1/2007 | Quy |
| 7,192,061 B2 | 3/2007 | Martin |
| D540,343 S | 4/2007 | Cummins |
| 7,223,365 B2 | 5/2007 | Von Der Goltz |
| 7,225,008 B1 | 5/2007 | Ward et al. |
| 7,226,461 B2 | 6/2007 | Boecker et al. |
| D551,243 S | 9/2007 | Young |
| 7,270,970 B2 | 9/2007 | Anderson et al. |
| 7,297,151 B2 | 11/2007 | Boecker et al. |
| 7,343,188 B2 | 3/2008 | Sohrab |
| 7,344,507 B2 | 3/2008 | Briggs et al. |
| 7,379,167 B2 | 5/2008 | Mawhirt et al. |
| 7,427,377 B2 | 9/2008 | Zanzucchi et al. |
| D599,373 S | 9/2009 | Kobayashi et al. |
| D601,257 S | 9/2009 | Berlinger et al. |
| 7,585,278 B2 | 9/2009 | Aceti et al. |
| D601,444 S | 10/2009 | Jones et al. |
| D601,578 S | 10/2009 | Poulet et al. |
| 7,682,318 B2 | 3/2010 | Alden et al. |
| D622,393 S | 8/2010 | Gatrall et al. |
| 7,803,123 B2 | 9/2010 | Perez et al. |
| 7,850,521 B2 | 12/2010 | Briggs et al. |
| 7,887,494 B2 | 2/2011 | Emery et al. |
| D642,191 S | 7/2011 | Barnett et al. |
| 8,012,103 B2 | 9/2011 | Escutia et al. |
| 8,012,104 B2 | 9/2011 | Escutia et al. |
| D654,926 S | 2/2012 | Lipman et al. |
| 8,184,273 B2 | 5/2012 | Dosmann et al. |
| 8,231,832 B2 | 7/2012 | Zanzucchi et al. |
| 8,303,518 B2 | 11/2012 | Aceti et al. |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,382,681 B2 | 2/2013 | Escutia et al. |
| D691,174 S | 10/2013 | Lipman et al. |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,969,097 B2 | 3/2015 | Emery et al. |
| 9,366,636 B2 | 6/2016 | Emery et al. |
| 9,603,562 B2 | 3/2017 | Aceti et al. |
| 9,636,051 B2 | 5/2017 | Emery et al. |
| 2001/0001034 A1 | 5/2001 | Douglas |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0022934 A1 | 2/2002 | Vogel et al. |
| 2002/0023852 A1 | 2/2002 | Mcivor et al. |
| 2002/0042594 A1 | 4/2002 | Lum et al. |
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |
| 2003/0028125 A1 | 2/2003 | Yuzhakov et al. |
| 2003/0039587 A1 | 2/2003 | Niermann |
| 2003/0083685 A1 | 5/2003 | Freeman et al. |
| 2003/0083686 A1 | 5/2003 | Freeman et al. |
| 2003/0116596 A1 | 6/2003 | Terasawa |
| 2003/0135166 A1 | 7/2003 | Gonnelli |
| 2003/0135333 A1 | 7/2003 | Aceti |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212347 A1 | 11/2003 | Sohrab |
| 2004/0010207 A1 | 1/2004 | Flaherty et al. |
| 2004/0030353 A1 | 2/2004 | Schmelzeisen-redeker et al. |
| 2004/0049219 A1 | 3/2004 | Briggs et al. |
| 2004/0059256 A1 | 3/2004 | Perez |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0096959 A1 | 5/2004 | Stiene et al. |
| 2004/0098009 A1 | 5/2004 | Boecker et al. |
| 2004/0102803 A1 | 5/2004 | Boecker et al. |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0236251 A1 | 11/2004 | Roe et al. |
| 2004/0238675 A1 | 12/2004 | Banaszkiewicz et al. |
| 2004/0259180 A1 | 12/2004 | Burke et al. |

(56) References Cited

U.S. PATENT DOCUMENTS

| | | |
|---|---|---|
| 2005/0010134 A1 | 1/2005 | Douglas et al. |
| 2005/0015020 A1 | 1/2005 | LeVaughn et al. |
| 2005/0070819 A1 | 3/2005 | Poux et al. |
| 2005/0096686 A1 | 5/2005 | Allen |
| 2005/0106713 A1 | 5/2005 | Phan et al. |
| 2005/0159678 A1 | 7/2005 | Taniike et al. |
| 2005/0187532 A1 | 8/2005 | Thurau et al. |
| 2005/0202567 A1 | 9/2005 | Zanzucchi et al. |
| 2005/0202733 A1 | 9/2005 | Yoshimura et al. |
| 2005/0215872 A1 | 9/2005 | Berner et al. |
| 2005/0215923 A1 | 9/2005 | Wiegel |
| 2005/0245844 A1 | 11/2005 | Mace et al. |
| 2005/0255001 A1 | 11/2005 | Padmaabhan et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0079809 A1* | 4/2006 | Goldberger ........ A61B 5/14532 600/576 |
| 2006/0117616 A1 | 6/2006 | Jones et al. |
| 2006/0122536 A1 | 6/2006 | Haar et al. |
| 2006/0135873 A1 | 6/2006 | Karo et al. |
| 2006/0155317 A1 | 7/2006 | List |
| 2006/0178600 A1 | 8/2006 | Kennedy et al. |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0281187 A1 | 12/2006 | Emery et al. |
| 2007/0017824 A1 | 1/2007 | Rippeth et al. |
| 2007/0078313 A1 | 4/2007 | Emery et al. |
| 2007/0078358 A1 | 4/2007 | Escutia et al. |
| 2007/0083131 A1 | 4/2007 | Escutia et al. |
| 2007/0179404 A1 | 8/2007 | Escutia et al. |
| 2007/0255181 A1 | 11/2007 | Alvarez-icaza et al. |
| 2007/0255302 A1 | 11/2007 | Koeppel et al. |
| 2008/0046831 A1 | 2/2008 | Imai et al. |
| 2008/0077048 A1 | 3/2008 | Escutia et al. |
| 2008/0194934 A1 | 8/2008 | Ray et al. |
| 2009/0156923 A1 | 6/2009 | Power et al. |
| 2009/0292489 A1 | 11/2009 | Burke et al. |
| 2009/0301899 A1 | 12/2009 | Hodges et al. |
| 2010/0010374 A1 | 1/2010 | Escutia et al. |
| 2010/0021947 A1 | 1/2010 | Emery et al. |
| 2010/0021948 A1 | 1/2010 | Lipman et al. |
| 2010/0095229 A1 | 4/2010 | Dixon et al. |
| 2010/0174211 A1 | 7/2010 | Frey et al. |
| 2010/0185120 A1 | 7/2010 | Sacherer et al. |
| 2010/0217155 A1 | 8/2010 | Poux et al. |
| 2011/0098599 A1 | 4/2011 | Emery et al. |
| 2011/0201909 A1 | 8/2011 | Emery et al. |
| 2012/0166090 A1 | 6/2012 | Lipman et al. |
| 2012/0296179 A1 | 11/2012 | Zanzucchi et al. |
| 2013/0158430 A1 | 6/2013 | Aceti et al. |
| 2013/0158432 A1 | 6/2013 | Escutia et al. |
| 2013/0172698 A1 | 7/2013 | Reynolds et al. |
| 2013/0274568 A1 | 10/2013 | Escutia et al. |
| 2014/0316301 A1 | 10/2014 | Escutia et al. |
| 2014/0336480 A1 | 11/2014 | Escutia et al. |
| 2014/0376762 A1 | 12/2014 | Lipman et al. |
| 2015/0037898 A1 | 2/2015 | Baldus et al. |

FOREIGN PATENT DOCUMENTS

| | | |
|---|---|---|
| DE | 103 02-501 A1 | 8/2004 |
| EP | 0103426 A2 | 3/1984 |
| EP | 0 256 806 A2 | 2/1988 |
| EP | 0 396-016 A2 | 11/1990 |
| EP | 0 396-016 A3 | 11/1990 |
| EP | 0 255-338 A2 | 2/1998 |
| EP | 1 266-607 A2 | 12/2002 |
| EP | 1 266-607 A3 | 12/2002 |
| EP | 1 360-934 A1 | 11/2003 |
| EP | 1 360-934 B1 | 11/2003 |
| EP | 1 486-766 A1 | 12/2004 |
| EP | 1 486-766 B1 | 12/2004 |
| EP | 1 529-489 A1 | 5/2005 |
| EP | 1 529-489 B1 | 5/2005 |
| EP | 1 769-735 A1 | 4/2007 |
| JP | 63-305841 A | 12/1988 |
| JP | 3-63570 | 3/1991 |
| JP | 03093189 A | 4/1991 |
| JP | 7-67861 A | 3/1995 |
| JP | 7-213925 A | 8/1995 |
| JP | 9-168530 A | 6/1997 |
| JP | 9-313465 A | 9/1997 |
| JP | 9-266889 A | 10/1997 |
| JP | 9-294737 A | 11/1997 |
| JP | 10-024028 A | 1/1998 |
| JP | 10-318970 A | 12/1998 |
| JP | 2000-116629 A | 4/2000 |
| JP | 2000-126161 A | 5/2000 |
| JP | 2000-168754 A | 6/2000 |
| JP | 2000-254111 A | 9/2000 |
| JP | 2001-159618 A | 6/2001 |
| JP | 2001-515203 A | 9/2001 |
| JP | 2001-305096 A | 10/2001 |
| JP | 2001-330581 A | 11/2001 |
| JP | 2002-502045 A | 1/2002 |
| JP | 2002-514453 A | 5/2002 |
| JP | 2002-168862 A | 6/2002 |
| JP | 2003-180417 A2 | 7/2003 |
| JP | 2004-000598 A | 1/2004 |
| JP | 2004-500948 A | 1/2004 |
| JP | 2004-117339 A | 4/2004 |
| JP | 2004-522500 A | 7/2004 |
| JP | 2004-528936 A | 9/2004 |
| JP | 2005-503538 A | 2/2005 |
| JP | 2005-087613 A | 4/2005 |
| JP | 2006-512969 A | 4/2005 |
| JP | 2005-525149 A | 8/2005 |
| JP | 2005-237938 A | 9/2005 |
| JP | 2005-525846 A | 9/2005 |
| JP | 2005-527254 A | 9/2005 |
| JP | 2006-512974 A | 4/2006 |
| JP | 2006-516723 A | 7/2006 |
| JP | 2006-521555 A | 9/2006 |
| JP | 2006-527013 A | 11/2006 |
| JP | 2007-067698 A | 3/2007 |
| JP | 2007-521031 A | 8/2007 |
| JP | 2007-311196 A | 11/2007 |
| WO | WO-88/07666 | 10/1988 |
| WO | WO-91/14212 A1 | 9/1991 |
| WO | WO-94/13203 A1 | 6/1994 |
| WO | WO-95/10223 A2 | 4/1995 |
| WO | WO-95/10223 A3 | 4/1995 |
| WO | WO-96/04857 A1 | 2/1996 |
| WO | WO-96/07907 A1 | 3/1996 |
| WO | WO-96/14026 A1 | 5/1996 |
| WO | WO-96/25088 A1 | 8/1996 |
| WO | WO-97/15227 A1 | 5/1997 |
| WO | WO-97/29847 A1 | 8/1997 |
| WO | WO-97/30344 A1 | 8/1997 |
| WO | WO-97/41421 A1 | 11/1997 |
| WO | WO-98/31275 A1 | 7/1998 |
| WO | WO-98/35225 A1 | 8/1998 |
| WO | WO-99/12008 A1 | 3/1999 |
| WO | WO-99/44508 A1 | 9/1999 |
| WO | WO-99/58051 A1 | 11/1999 |
| WO | WO-00/09184 A1 | 2/2000 |
| WO | WO-00/13573 A1 | 3/2000 |
| WO | WO-00/14269 A1 | 3/2000 |
| WO | WO-00/14535 A1 | 3/2000 |
| WO | WO-00/18449 A2 | 4/2000 |
| WO | WO-00/18449 A3 | 4/2000 |
| WO | WO-00/19185 | 4/2000 |
| WO | WO-00/36400 A1 | 6/2000 |
| WO | WO-00/42422 A1 | 7/2000 |
| WO | WO-00/74763 A2 | 12/2000 |
| WO | WO-00/74763 A3 | 12/2000 |
| WO | WO-00/78208 A1 | 12/2000 |
| WO | WO-01/16575 A1 | 3/2001 |

(56) References Cited

FOREIGN PATENT DOCUMENTS

| WO | WO-01/52727 | A1 | 7/2001 |
|---|---|---|---|
| WO | WO-01/64105 | A1 | 9/2001 |
| WO | WO-01/64105 | C2 | 9/2001 |
| WO | WO-01/72220 | A1 | 10/2001 |
| WO | WO-01/80728 | A1 | 11/2001 |
| WO | WO-01/85233 | A2 | 11/2001 |
| WO | WO-01/85233 | A3 | 11/2001 |
| WO | W0-01/91634 | A3 | 12/2001 |
| WO | WO-01/91634 | A2 | 12/2001 |
| WO | WO-02/00101 | A2 | 1/2002 |
| WO | WO-02/00101 | A3 | 1/2002 |
| WO | WO-02/49507 | A1 | 6/2002 |
| WO | WO-02/49509 | A2 | 6/2002 |
| WO | WO-02/49509 | A3 | 6/2002 |
| WO | WO-02/082052 | A2 | 10/2002 |
| WO | WO-02/082052 | A3 | 10/2002 |
| WO | WO-02/093144 | A1 | 11/2002 |
| WO | WO-02/100251 | A2 | 12/2002 |
| WO | WO-02/100251 | A3 | 12/2002 |
| WO | WO-02/101359 | A2 | 12/2002 |
| WO | WO-02/101359 | A3 | 12/2002 |
| WO | WO-2003/030984 | A1 | 4/2003 |
| WO | WO-2003/066128 | A2 | 8/2003 |
| WO | WO-2003/066128 | A3 | 8/2003 |
| WO | WO-2003/070099 | A1 | 8/2003 |
| WO | WO-2003/071940 | A1 | 9/2003 |
| WO | WO-2003/071940 | C1 | 9/2003 |
| WO | WO-2004/062499 | A1 | 7/2004 |
| WO | WO-2004/062500 | A1 | 7/2004 |
| WO | WO-2004/062500 | C1 | 7/2004 |
| WO | WO-2004/064636 | A1 | 8/2004 |
| WO | WO-2004/085995 | A2 | 10/2004 |
| WO | WO-2004/085995 | A3 | 10/2004 |
| WO | WO-2004/091693 | A2 | 10/2004 |
| WO | WO-2004/091693 | A3 | 10/2004 |
| WO | WO-2005/006939 | A2 | 1/2005 |
| WO | WO-2005/006939 | A3 | 1/2005 |
| WO | WO-2005/009238 | A1 | 2/2005 |
| WO | WO-2005/018709 | A2 | 3/2005 |
| WO | WO-2005/018709 | A3 | 3/2005 |
| WO | WO-2005/084546 | A2 | 9/2005 |
| WO | WO-2005/084546 | A3 | 9/2005 |
| WO | WO-2005/085995 | A1 | 9/2005 |
| WO | WO-2006/138226 | A2 | 12/2006 |
| WO | WO-2006/138226 | A3 | 12/2006 |
| WO | WO-2007/041062 | A2 | 4/2007 |
| WO | WO-2007/041062 | A3 | 4/2007 |
| WO | WO-2007/041063 | A2 | 4/2007 |
| WO | WO-2007/041063 | A3 | 4/2007 |
| WO | WO-2007/041244 | A2 | 4/2007 |
| WO | WO-2007/041244 | A3 | 4/2007 |
| WO | WO-2007/041287 | A2 | 4/2007 |
| WO | WO-2007/041287 | A3 | 4/2007 |
| WO | WO-2007/041355 | A2 | 4/2007 |
| WO | WO-2007/041355 | A3 | 4/2007 |
| WO | WO-2008/027319 | A2 | 3/2008 |
| WO | WO-2008/027319 | A3 | 3/2008 |
| WO | WO-2009/145920 | A1 | 12/2009 |
| WO | WO-2009/148624 | A1 | 12/2009 |
| WO | WO-2009/148626 | A1 | 12/2009 |
| WO | WO-2011/065981 | A1 | 6/2011 |
| WO | WO-2011/162823 | A1 | 12/2011 |
| WO | WO-2013/020103 | A1 | 2/2013 |
| WO | WO-2014/205412 | A1 | 12/2014 |

OTHER PUBLICATIONS

ADA (Jan. 1994). "Self-Monitoring of Blood Glucose," Consensus Statement *Diabetes Care* 17(1):81-86.

Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.

Anonymous. (Jun. 23, 1998). Taking the "Ouch" Out of Needles: Arrays of "Microneedles" Offer New Techniques for Drug Delivery, *Science Daily*, located at <http:www.sciencedaily.com/releases/1998/06/980623045850.htm>, last visited Jan. 14, 2014, 3 pages.

Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.

Chase, H.P. et al. (Feb. 2001). "Continuous Subcutaneous Glucose Monitoring in Children with Type 1 Diabetes," *Pediatrics* 107(2):222-226.

Clarke, W.L. et al. (Sep.-Oct. 1987). "Evaluating Clinical Accuracy of Systems for Self-Monitoring of Blood Glucose," *Diabetes Care* 10(5):622-628.

Clarke, W.L. et al. (1981). "Evaluation of a New Reflectance Photometer for Use in Home Blood Glucose Monitoring," *Diabetes Care* 4(5):547-550.

Collison, M.E. et al. (Sep. 1999). "Analytical Characterization of Electrochemical Biosensor Test Strips for Measurement of Glucose in Low-Volume Interstitial Fluid Samples,"*Clinical Chemistry* 45(9): 1665-1673.

Cox, D.J. et al. (Jun. 1997). "Understanding Error Grid Analysis," *Diabetes Care* 20(6):911-912.

D'Arrigo, T.D. (Mar. 2000). "GlucoWatch Monitor Poised for Approval," *Diabetes Forecast*, 53(3):43-44.

Extended European Search Report dated Jul. 18, 2013, for EP Application No. 06 772 943.4, filed on Jun. 13, 2006, 7 pages.

Extended European Search Report dated Aug. 27, 2012, for European Patent Application No. 09 758 789.3, filed on Jun. 8, 2009, 13 pages.

Final Office Action dated Oct. 15, 2009, for U.S. Appl. No. 11/239,122, filed on Sep. 30, 2005, 13 pages.

Final Office Action dated Aug. 14, 2012, for U.S. Appl. No. 13/037,089, filed on Feb. 28, 2011, 14 pages.

Final Office Action dated Sep. 23, 2013, for U.S. Appl. No. 13/037,089, filed on Feb. 28, 2011, 14 pages.

Feldman, B. et al. (2000). "FreeStyle™: A Small-Volume Electrochemical Glucose Sensor for Home Blood Glucose Testing," *Diabetes Technology and Therapeutics*, 2(2):221-229.

International Search Report dated Jan. 16, 2008, for PCT Application No. PCT/US2006/022840, filed on Jun. 13, 2006, 1 page.

Johnson, R.N. et al. (Jan. 1998). "Accuracy of Devices Used for Self-Monitoring of Blood Glucose," *Annals of Clinical Biochemistry* 35(1):68-74.

Johnson, R.N. et al. (Jan. 1999). "Analytical Error of Home Glucose Monitors: A Comparison of 18 Systems," *Annals of Clinical Biochemistry* 36(1):72-79.

Johnson, R.N. et al. (2001). "Error Detection and Measurement in Glucose Monitors," *Clinica Chimica Acta* 307:61-67.

Kumetrix, Inc. (Dec. 1999). "Painless Blood Glucose Monitoring, Courtesy of the Mosquito," *Start-Up* pp. 27-28.

Lee, S-C. (Jun. 1999). "Light Scattering by Closely Spaced Parallel Cylinders Embedded in a Finite Dielectric Slab," *Journal of the Optical Society of America A* 16(6):1350-1361.

McGarraugh, G. et al. (2001). "Physiological Influences on Off-Finger Glucose Testing," *Diabetes Technology & Therapeutics* 3(3):367-376.

McNichols, R.J. et al. (Jan. 2000). "Optical Glucose Sensing in Biological Fluids: An Overview," *Journal of Biomedical Optics*, 5(1):5-16.

Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4): 1165-1171.

Medline Plus. (Jun. 17, 2008). , Medical Encyclopedia, Monitor Blood Glucose-Series: Part 1-4, 6 pages.

Neeley, W.E. et al. (1981). "An Instrument for Digital Matrix Photometry," *Clinical Chemistry* 27(10):1665-1668.

Neeley, W.E. (1983). "Reflectance Digital Matrix Photometry," *Clinical Chemistry* 29(6):1038-1041.

Neeley, W.E. (1983). "Multilayer Film Analysis for Glucose in 1-µL Samples of Plasma," *Clinical Chemistry* 29(12):2103-2105.

(56) References Cited

OTHER PUBLICATIONS

Neeley, W.E. (1988). "A Reflectance Photometer with a Square Photodiode Array Detector for Use on Multilayer Dry-Film Slides," *Clinical Chemistry* 34(11):2367-2370.
Non-Final Office Action dated Mar. 19, 2009, for U.S. Appl. No. 11/239,122, filed Sep. 30, 2005, 15 pages.
Non-Final Office Action dated Sep. 1, 2010, for U.S. Appl. No. 11/239,122, filed Sep. 30, 2005, 15 pages.
Non-Final Office Action dated Sep. 13, 2011, for U.S. Appl. No. 13/037,089, filed Feb. 28, 2011, 14 pages.
Non-Final Office Action dated Feb. 28, 2013, for U.S. Appl. No. 13/037,089, filed Feb. 28, 2011, 12 pages.
Non-Final Office Action dated Apr. 10, 2014, for U.S. Appl. No. 13/037,089, filed Feb. 28, 2011, 14 pages.
Non-Final Office Action dated May 29, 2015, for U.S. Appl. No. 14/614,177, filed Feb. 4, 2015, 13 pages.
Notice of Allowance dated Sep. 18, 2014, for U.S. Appl. No. 13/037,089, filed Feb. 28, 2011, 9 pages.
Notice of Allowance dated Feb. 16, 2016, for U.S. Appl. No. 14/614,177, filed Feb. 4, 2015, 7 pages.
Otto, E. et al. (2000). "An Intelligent Diabetes Software Prototype: Predicting Blood Glucose Levels and Recommending Regimen Changes," *Diabetes Technology and Therapeutics* 2(4):569-576.
Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.
Princen, H.M. (May 1969). "Capillary Phenomena in Assemblies of Parallel Cylinders, I. Capillary Rise Between Two Cylinders," *Journal of Colloid and Interface Science* 30(1):69-75.
Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.
Rebrin, K. et al. (Sep. 1999). "Subcutaneous Glucose Predicts Plasma Glucose Independent of Insulin: Implications for Continuous Monitoring," *American Journal of Physiology* 277(3):E561-E571.
Smart, W.H. et al. (2000). "The Use of Silicon Microfabrication Technology in Painless Glucose Monitoring," *Diabetes Technology & Therapeutics* 2(4):549-559.
Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.
Tietz, N.W. (1986).Textbook of Clinical Chemistry, W. B. Saunders Company, pp. 1533 and 1556.
Trinder, P. (1969). "Determination of Glucose in Blood Using Glucose Oxidase with an Alternate Oxygen Acceptor," *Annals of Clinical Biochemistry* 6:24-28.
Written Opinion of the International Searching Authority dated Jan. 16, 2008, for PCT Application No. PCT/US2006/022840, filed on Jun. 13, 2006, 3 pages.
Yum, S. I. et al. (Nov. 1, 1999). "Capillary Blood Sampling for Self-Monitoring of Blood Glucose," Diabetes Technology & Therapeutics, 1(1):29-37.
Non-Final Office Action dated Dec. 19, 2016, for U.S. Appl. No. 13/566,886, filed Aug. 3, 2012, 18 pages.
Extended European Search Report dated Nov. 8, 2016 by the European Patent Office for Application No. 16167087.2, filed Aug. 3, 2012, 7 pages.

\* cited by examiner

ANALYTE DETECTION DEVICES AND METHODS WITH HEMATOCRIT/VOLUME CORRECTION AND FEEDBACK CONTROL

CROSS-REFERENCE TO RELATED APPLICATIONS

The present application is a continuation of U.S. patent application Ser. No. 14/614,177, filed Feb. 4, 2015, which issued as U.S. Pat. No. 9,366,636 on Jun. 14, 2016, which is a continuation of U.S. patent application Ser. No. 13/037,089, filed Feb. 28, 2011, which issued as U.S. Pat. No. 8,969,097 on Mar. 3, 2015, and which is a continuation of U.S. patent application Ser. No. 11/239,122, filed Sep. 30, 2005, which claims priority pursuant to 35 U.S.C. § 119(e) to U.S. Patent Application No. 60/689,546 filed Jun. 13, 2005, the entire content of each of which is incorporated herein by reference.

FIELD OF THE INVENTION

The present invention is directed to techniques and devices for detection of the presence and/or concentration of an analyte.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

According to the American Diabetes Association, diabetes is the fifth-deadliest disease in the United States and kills more than 213,000 people a year, the total economic cost of diabetes in 2002 was estimated at over $132 billion dollars, and the risk of developing type I juvenile diabetes is higher than virtually all other chronic childhood diseases.

A critical component in managing diabetes is frequent blood glucose monitoring. Currently, a number of systems exist for self-monitoring by the patient. One such system may be termed a photometric system or method. In such systems, the first step is to obtain the sample of aqueous fluid containing an analyte to be assayed, usually whole blood or fractions thereof. The sample of blood may be obtained by a finger stick or other means.

The fluid sample is then contacted with an assay pad or membrane. Contact is generally achieved by moving the assay pad or membrane into contact with the liquid sample on the surface of the patient's skin. Following application to the pad or membrane, the target analyte present in the sample passes through the assay pad or membrane by capillary, wicking, gravity flow and/or diffusion mechanisms. Chemical reagents present in the pad or membrane react with the target analyte producing a light absorbing reaction product, or color change.

The assay pad or membrane is then inserted into a monitor where an optical measurement is then made of this color change. In those embodiments where the optical measurement is a reflectance measurement, a surface of the assay pad or membrane is illuminated with a light source. Light is reflected from the surface of the assay pad or membrane as diffuse reflected light. This diffuse light is collected and measured, for example by the detector of a reflectance spectrophotometer. The amount of reflected light is then related to the amount of analyte in the sample; usually the amount of light reflected off the surface of the assay pad or membrane is an inverse function of the amount of analyte contained in the sample.

An algorithm is employed to determine analyte concentration contained in the sample based on the information provided by the detector. Representative algorithms that may be employed where the analyte of interest is glucose and the fluid sample is whole blood are disclosed, for example, in U.S. Pat. Nos. 5,049,487; 5,059,394; 5,843,692 and 5,968,760; the disclosures of which are incorporated herein by reference.

Glucose monitoring technology that relies on the photometric method of quantifying the glucose concentration in whole blood may be subject to errors associated with variations in hematocrit level, or concentration of red blood cells within the blood sample. Various methods have been employed to ensure the accuracy and repeatability of measured glucose concentration using the photometric method across a typical range of hematocrit levels. A normal hematocrit level is 42-54% for men and 36-48% for women. Overall, the normal range is from 36-54%, but for a variety of reasons, those who regularly test their glucose concentrations may have hematocrit levels even lower (anemia) or higher (polycythemia) than these normal ranges. This presents a challenge for the development of accurate glucose monitoring. This is because the meter is typically designed or calibrated assuming the sample will contain a hematocrit level somewhere in the normal range. Diabetics and clinicians make critical medical decisions in the management of their disease based on the readings provided by these meters. Thus, it would be advantageous to have a photometric quantification method that is more accurate across a broader range of hematocrit levels.

Additionally, glucose monitors typically require that the user supply a sufficient quantity of whole blood for an accurate reading. This volume has been around 10 microliters or more in the past, but with the development of newer quantification technologies, the minimum volume has been brought to as low as 1 microliter for photometric meters. This has reduced the burden on diabetics in their testing by reducing the depth of the lancing and the effort to milk a relatively large amount of blood from their lancing site. Again, the calibration of the meter is developed with the assumption that this minimum supply has been delivered to the test strip. If the user has not supplied a sufficient amount, then the meter generally displays an error code and the user must test again. Further, a user may supply more than the typical amount of blood to the test strip, which may lead to an inaccurate result if the calibration of the strip is volume sensitive. It would be advantageous for a photometric meter to have the ability to evaluate and adjust its internal calibration by detecting the amount of fluid supplied to the reagent strip, and applying an appropriate calibration parameter specifically chosen for that volume.

The development of a fully integrated glucose meter system requires incorporating the processes of skin lancing, transfer of blood to the reagent test strip, and quantification of whole blood glucose all in a single device. Such systems may not require any user intervention at all during the quantification process as long as sufficient sample volume is obtained. An automated catalyst, such as heat, vacuum, or pressure may be utilized to obtain a sample of body fluid, or whole blood.

One such device relies on the application of a specific magnitude and duration of a partial vacuum to the skin in order to facilitate the acquisition of a minimum required sample volume. For some individuals, this pre-programmed amount or duration of vacuum may be appropriate. For others, this pre-programmed catalyst may produce either an insufficient or excessive amount of blood, as well as other undesired outcomes, such as excessive bruising (for those with fragile capillary networks), an unnecessary delay in obtaining results (for fast bleeding individuals), as well as excessive residual blood left on the skin. Thus, it would be advantageous if the sample quantification detector could also determine in real-time whether or not a sufficient sample volume has been obtained for an accurate reading, and provide this information as feedback to control the magnitude and/or duration of a catalyst. This feedback driven control would be a significant advantage for integrated glucose monitoring technology.

Photometric assay pads or membranes for analyte concentration measurements typically produce a circular or linear spot when the chemical reagents contained therein react with a fluid containing a specific analyte, such as glucose, within whole blood. An ideal spot may be defined as one in which the color across the spot is uniform and indicative of the concentration of the analyte. A spot which is not ideal may be manifest in one or more of the following ways: non-uniformity of the primary color (e.g., variations in the intensity of blue); presence of non-primary color, such as red, which may be associated with the presence and/or lysis of blood cells, and the above color variations may be distributed randomly or non-uniformly across the spot.

For a variety of reasons, the quality of a spot developed as a result of an analyte reacting with the reagent membrane may not be ideal as described above. Such reasons may include one or more of: flaws or manufacturing variations in the membrane structure; variations in the concentration of the reagent enzyme; mishandling of the membrane during manufacturing; and unintended chemical reactions between the fluid and/or analyte and the reagent structure and/or membrane chemistry (such as another medical drug within the blood sample reacting with the reagent enzyme).

Most devices on the market cannot detect or correct for low quality spots. Their sensors, typically one or more photodiodes, do not have the ability to discretely analyze the flaws within a reagent spot. Thus, there exists a risk that these systems may not provide an accurate reading in circumstances of a non-ideal spot.

SUMMARY OF THE INVENTION

According to the present invention, the state of the art has been advanced through the provision of arrangements, devices and techniques such as those described further herein, for accurately, efficiently, and economically determining the presence and/or concentration of an analyte. According to the present invention, the state of the art has been advanced, especially, but not exclusively, within the context of personal glucose monitoring devices and techniques. Additionally, or alternatively, according to the present invention arrangements, devices and techniques are provided which may overcome one or more of the above-mentioned shortcomings associated with conventional systems and methods.

Devices and methods are contemplated that may employ a detector comprising an array of detector elements or pixels to detect color change or intensity of reflected light associated with a photometric chemical reaction between the analyte and reagent chemistry. Optionally, the detector elements comprise CMOS-based detector elements. In particular, the CMOS detector elements help correct for differences in hematocrit levels and/or volumes associated with samples under analysis. An additional aspect of the present invention provides for CMOS-based detector elements that can provide feedback control for a connected device that performs automated whole blood sampling and detection of an analyte. In yet another aspect of the present invention, feedback from CMOS detection elements is used to compensate for non-ideal reaction spot characteristics.

According to one aspect, the present invention provides a device for monitoring the concentration of an analyte present in bodily fluid, the device comprising a detector, the detector comprising a detector element or pixel, the element or pixel comprising a CMOS sensor, a CCD sensor, a photodiode or an infrared sensor, including both near-field and mid-field infrared sensors. Other sensing systems also contemplated within the scope of the present invention include infrared, ultraviolet and fluorescent sensing systems and electrochemical sensing systems, including reagentless sensing approaches.

It is therefore to be understood that reference herein to the detector array of the present invention may include any suitable detector element(s). The present invention is thus not limited to embodiments of the invention including CMOS or CCD detector elements, photodiodes, infrared, fluorescent, ultraviolet or electrochemical detector elements.

It is to be understood that the detector array is not limited only to linear arrays. Non-linear arrays, such as polar or area arrays, are also contemplated by the present invention.

It is to be understood that reference herein to first, second, third and fourth components (etc.) does not limit the present invention to embodiments where each of these components is physically separable from one another. For example, a single physical element of the invention may perform the features of more than one of the claimed first, second, third or fourth components. Conversely, a plurality of separate physical elements working together may perform the claimed features of one of the claimed first, second, third or fourth components. Similarly, reference to first, second (etc.) method steps does not limit the invention to only separate steps. According to the invention, a single method-step may satisfy multiple steps described herein. Conversely, a plurality of method steps could, in combination, constitute a single method step recited herein.

According to an aspect of the present invention, there are provided devices, arrangements and methods for quantifying the concentration of an analyte present in bodily fluid, comprising: an assay pad comprising at least one chemical reagent capable of producing a detectable signal in the form of a reaction spot upon reaction with the analyte; a light source; a detector; a processor; and a memory in communication with the processor, the memory comprising: (a) at least one value indicative of one or more of: (i) the level of hematocrit contained in the sample; (ii) the volume of the sample applied to the assay pad; or (iii) imperfections present in the reaction spot; and (b) at least one algorithm for calculating the concentration of the analyte contained in the sample.

According to a further aspect of the present invention, there are provided devices, arrangements and methods for quantifying the concentration of an analyte present in bodily fluid, comprising: providing an assay pad comprising at least one chemical reagent; introducing a sample onto the assay pad; producing a detectable signal in the form of a reaction spot upon reaction of the at least one chemical reagent with the analyte; generating a signal based on light reflected off the assay pad; calculating at least one value indicative to one or more of: (i) the level of hematocrit contained in the sample; (ii) the volume of the sample applied to the assay pad; or (iii) imperfections present in the reaction spot; and calculating the concentration of analyte contained in the sample by factoring in the at least one value.

According to the above, the device may comprise a glucose meter integrating some or all of the above-described features. The integrated device may be configured to perform at least one such photometric analysis before reloading disposable components thereof becomes necessary. The integrated device may be handheld or wearable. The integrated device may be in the general form of a wristwatch.

According to the present invention, the detector elements may comprise CMOS-based detector elements. Moreover, the detector array may be in the form of a linear array of CMOS-based detector elements or pixels.

According to the present invention, an integrated device may include means for extracting a sample of bodily fluid and can comprise a skin piercing member and the application of one or more of: (i) vacuum; (ii) positive pressure; and (iii) heat.

According to the present invention, as described above, the device may further comprise a computer-readable medium, the medium comprising at least one of an algorithm and a look-up table. According to the present invention, the device may further comprise a microprocessor controller.

The above-described invention may further comprise at least one of a light source, one or more lenses, one or more light transmission elements (e.g. optical fibers), optical diffusers and optical filters.

In certain embodiments of the above-described invention, the assay pad may comprise at least one chemical reagent that produces a color change defining a reaction spot upon reaction with the analyte.

BRIEF DESCRIPTION OF THE DRAWINGS

The preferred embodiments are illustrated in the drawings in which like reference numerals refer to the like elements and in which.

DETAILED DESCRIPTION OF THE INVENTION

Figure 1:
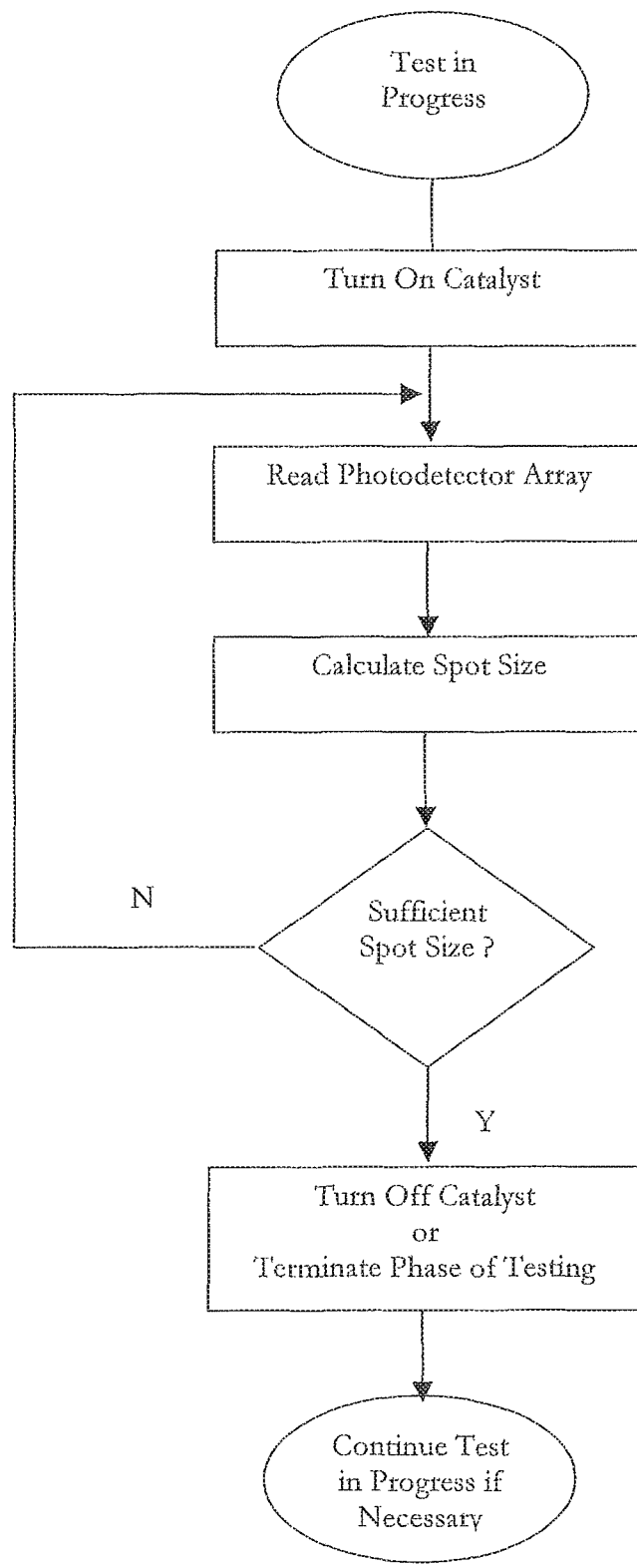
FIG. 1 is a flow diagram of a mode of operation according to certain aspects of the present invention.

Exemplary arrangements and methods for the detection and measurement of the presence and/or concentration of a target analyte, such as glucose, bilirubin, alcohol, controlled substances, toxins, hormones, proteins, etc., will now be described.

In broader aspects, the current invention provides the ability to correct for broad variations in sample hematocrit levels in the measurement of an analyte, such as glucose, during the course of the test. The invention takes advantage of an imaging array of detectors to perform this correction and does not require any additional hardware. In other words, no other distinct sensors or detectors, other than the imaging array, are required to calculate the correction. The very sensor that is used to quantify the analyte within the sample may also correct for hematocrit. Strategic algorithms that process the data from the imaging array provide real-time or near real-time information about the sample hematocrit level. Thus, more accurate results, regardless of the hematocrit level of the user, may be obtained via correction based on the hematocrit level of the sample.

The current invention may also use appropriate algorithms to permit real-time sensing of the amount of sample volume delivered to an assay pad. With this information, appropriate calibration parameters may be selected corresponding to the actual delivered volume. To correct for sample volume, algorithms similar to those used for hematocrit correction may be used, where volume is substituted for hematocrit and a unique formulation and corresponding constants are determined.

The present invention offers the flexibility to improve the accuracy of measured glucose for a broad range of sample volumes that are typically delivered to the assay pad of the meter system. In addition, sampling catalysts such as vacuum, heat, pressure, etc. may be implemented or provided automatically by the device to help ensure sufficient sample volume is collected and analyzed. The invention provides information to the meter system to know when and how much of the catalyst is sufficient. Since the invention can measure or estimate the volume of the sample delivered to the assay pad, it can also provide feedback to start, maintain or terminate the catalysts, as well as increase or decrease the magnitude of the catalyst, based on this measured volume. This offers the advantage of adapting the device function to the user's real-time skin physiology, minimizing the risks associated with the catalysts (bruising, scarring, excessive bleeding), reducing the energy consumed by the system, and reducing the chance of a wasted test operation (and the associated user's time, battery supply, and cost of test strip) by ensuring a minimum sample volume is obtained, as well as minimizing the overall time to get a result from the system.

According to additional broad aspects, the present invention can process data received from the detector array to compensate for irregularities or imperfections present in a reaction spot in order to improve accuracy of the analyte concentration method. The present invention includes devices, arrangements and methods that include any of the above referenced aspects individually, as well as combinations of some or all of these aspects.

The current invention may employ a linear CMOS imaging detector array. Contrary to other approaches that describe the use of 2-D CCD imaging detector arrays, the linear CMOS array detects light across a single row of optical detectors (pixels) whose output is proportional to the amount of light incident to the pixel. Linear detector arrays offer an advantage over 2-D imaging systems in simplicity and efficiency in processing the image information as long as the expected location of reagent chemistry reaction or reagent spot is known and the associated light, which may be supplied by an LED, is reflected from this area and is imaged appropriately by the CMOS array.

The CMOS detector array may have an overall size that is comparable to the size of the assay pad and the expected range of spot sizes that develop on the pad. According to one alternative, the detector can be larger than the size of the pad. This construction can allow wider tolerances in the relative position of the assay pad and the detector, and provide for additional in-process error detection and recovery (e.g., detecting or correcting for assay pad motion).

In addition to light sources such as LED's, various optical components such as lenses, diffusers, light pipes, etc. may be integrated into the system to optimize the image size and resolution. Such a system may utilize a commercially available linear CMOS detector array such as part # TSL1401R or TSL1401CS; from TAOS, Plano, Tex. This detector has 128 pixels across an array of ~19 mm in length. Light reflected off of white surfaces, such as an unreacted reagent pad, and received by the CMOS detector results in a signal from each pixel that is conditioned to produce a near maximum response up to 5 volts. Darker surfaces, such as from a color change associated with a reagent spot, will produce lower voltage response for each pixel depending on the reagent chemistry, light source, optical path, and ultimately, the concentration of the analyte (e.g., glucose).

A number of different arrangements comprising a quantification member, such as an assay pad, a sensor or detector, and one or more additional components are contemplated by the present inventions. Additional exemplary arrangements are described in U.S. application Ser. No. 10/394,230, entitled ANALYTE CONCENTRATION DETECTION DEVICES AND METHODS, the entire content of which is incorporated by reference herein.

When coupled with an assay pad containing a photometric reagent, the sensor detects the change in color of the pad, and the output is processed as a change in voltage relative to that of the original reagent color. Typically, about 10-50% of the pixels across the array are sufficient to resolve a spot of color change, but this can depend on a variety of factors, including CMOS sensor design, sample volume size, reagent dynamics, and the optical path between the pad and sensor.

Since the arrangements and techniques of the present invention can perform the assay without all of the pixels in the sensor array being in optical registry with the reagent spot, it is contemplated by the present invention to utilize these free pixels in one or more possible ways. For example, a second assay may be performed at a different area of the same assay pad, or on separate assay pad, at a location corresponding to the aforementioned unused pixels. The unused pixels may be used for calibration or as a control. For instance, a control solution having a known concentration of analyte may be introduced in the area of the assay pad, or onto a separate pad, in the area of the unused pixels. The control solution reacts with the reagent and the signal produced by pixels can be calibrated in accordance with the known analyte concentration. According to another alternative, a means for calibrating the reagent for lot information may be provided in the area of the unused pixels, thereby eliminating the need for the user to set reagent lot calibration codes. A similar arrangement and technique would be to utilize a standard color in registry with the unused pixels that produces a known reflectance signal. Upon reading this known signal, the arrangement, via a microprocessor and associated software and electronic components, can verify whether or not the device is functioning properly.

According to certain embodiments, sensor data can be acquired with an analog-to-digital capture device, such as a PC board, and processed as a linear dimension data array whose size corresponds to the number of pixels in the imaging array, such as 128 or 256 pixels. This data array will change over time as the reaction between the analyte (glucose) and the reagent enzymes develops, reaches saturation and begins to dry out.

According to one embodiment, the current invention incorporates an algorithm for processing the information in the data array over time to detect and correct for the hematocrit in the blood sample. The rate of color change over time across the detector array, and thus rate of change in signal of the data array, is dependent upon the relative amount of plasma in the sample. A relatively high plasma content in a given sample size will cause the sample to react with the reagent chemistry faster and develop a change in color more quickly than a relatively smaller plasma content. Since hematocrit level is inversely proportional to plasma content, the rate of color change can be scaled inversely to hematocrit level.

The relation between rate of color change and hematocrit level will depend upon a variety of variables, including the volume of the sample delivered to the assay pad as well as the inherent reagent chemistry, optical path, light source and detector array. Consequently, a unique correlation calibration between color change rate as detected by the CMOS imager and blood hematocrit level can be empirically determined and programmed into a memory device as a lookup table, or calculation.

Exemplary, non-limiting algorithm formulations to accomplish the above include:

1. Hct $\alpha$ $\delta A(x,t)/\delta t$; where Hct=hematocrit, $\alpha$ implies proportional to, $\delta/\delta t$=is the partial derivative with respect to time (a measure of rate of change), and $A(x,t)$ is a measure of the array signal strength in the sensor at position x at time t.

Proportionality may be linear and of the form Hct=m($\delta A(x,t)/\delta t$)+C; where m and C are constants determined empirically. Hematocrit proportionality correction may also be better represented by polynomial, exponential, power or other functions.

2. Hematocrit $\alpha$ $\delta A(x,t)/\delta x$; where Hct and $\alpha$ are as defined above, and $\delta/\delta x$=is the partial derivative with respect to position x.

Again, proportionality may be linear and of the form Hct=m($\delta A(x,t)/\delta x$)+C; where m and C are constants determined empirically. Proportionality may also be non-linear and represented by logarithmic, polynomial, exponential or other equations.

3. Hematocrit $\alpha$ $\delta A(x,t)/\delta x \delta t$; where Hct and $\alpha$ are as defined above, and $\delta/\delta x \delta t$=is the partial derivative with respect to position x and time t.

4. Hematocrit $\alpha$ $\delta^2 A(x,t)/\delta^2 x \delta^2 t$; where Hct and $\alpha$ are as defined above, and $\delta^2/\delta^2 x \delta^2 t$=is the second order partial derivative with respect to position x and time t.

Pixel position x ranges from the lower to upper limits and in the case of a 256 pixel array, would range from 1 to 256. For a variety of reasons, the algorithm may be limited to the evaluation of specific positions or ranges within the array, such as between x=x_lower and x=x_upper, where x_lower may be 40 and x_upper may be 80.

Time t as referred to in these algorithms can refer to the time elapsed between known events within the analyte quantification process. For example, t=0 may be defined at the point in which blood is first presented to the reagent membrane, or when the imaging array first detects a predetermined threshold change corresponding to the arrival of the analyte to the reagent membrane.

Array signal strength $A(x,t)$ corresponds to a measure of the color of the reagent membrane. Typically, this signal is initially processed as a voltage or a current. Those skilled in the art of photometric reagent signal process will appreciate that subsequent transformation of this data into a measure of normalized reflectance R and/or to absorption via the well-known calculation of K/S may be represented by $A(x,t)$. For example:

K/S $(x,t)=(1-R)^2/2R$; where $R=A(x,t)_{Reacted}/A(x,t)_{Unreacted}$, where $A(x,t)_{Unreacted}$ refers to the array signal corresponding to the reagent membrane prior to any reaction with the analyte, and $A(x,t)_{Reacted}$ the array signal corresponding to the membrane as it reacts with the analyte at array position x at time t.

Those skilled in the art will appreciate that combinations of these and/or other similar algorithms would mathematically capture the relation between hematocrit and the rate of change of spot development in the membrane. Furthermore, the skilled reader would appreciate that the proportionality constants (m and C) are dependent upon the conditions of the reagent membrane (material, chemistry, lighting), the hardware and software specifications, and the nature and method in which the analyte is delivered to the membrane.

Thus, the appropriate calibration factor-relating reflected light to glucose concentration would then be chosen based on the hematocrit level. When the consumer uses the device, the meter detects color change and applies the correct calibration factor for the user's hematocrit level to the calculation of glucose content made by an algorithm also contained in the same, or a different memory device.

As an example of the above, if the glucose calibration curve is of the form:

R=m×[Glucose Concentration]+b; where R=the as-measured reflected light signal, and m and b are empirically determined constants.

A corrected signal $R_c$, could be derived from a look-up table of correction factors, $F_h$, as a function of hematocrit level:

$$R_c = F_h \times R$$

This corrected signal would then be substituted into the above equation to calculate the hematocrit-adjusted glucose concentration.

Processing the data generated by the change in color caused by the reaction between the analyte and reagent chemistry in conjunction with the speed and capacity of today's microprocessors would not add to the required time to process the sample, yet would substantially increase the accuracy and reduce the variability for analyte concentration measurements associated with different whole blood hematocrit levels.

Various alternatives and modifications to the above-described embodiment related to detector data analysis to determine hematocrit levels are possible. For example, such alternatives and modifications include one or more of: evaluating the rate of pixel signal changes with respect to time; evaluating the rate of pixel change with respect to time and with respect to associated pixels that also are changing (i.e., spatial and temporal rate of change); evaluating the rate of pixel change with respect to time for an individual pixel; evaluating the rate of pixel change with respect to time for multiple pixels; evaluating the rate of pixel change with respect to time for the pixel that detects the largest change in color when enzymatic reaction and color change is complete; evaluating the rate of pixel change with respect to time for the pixel that detects the largest change in color during the ongoing enzymatic reaction; evaluating the rate of pixel change with respect to time for the pixel that detects the largest change in color after a lapse of a predetermined amount of time before any enzymatic reaction has actually occurred; and evaluating the resolved volume of the sample (as described earlier) at a specific time for which a fixed, prescribed amount of blood has been delivered to the reagent pad (since measured sample size is proportional to plasma volume, which is inversely proportional to hematocrit).

Using the aforementioned detector array, the invention also contemplates novel arrangements, devices and methods for quantifying, in real-time, the amount of sample delivered to an analyte quantification member, such as an assay pad. This method takes advantage of the discrete data provided by individual detector elements or pixels. As a reaction spot begins to develop in the assay pad, the system described earlier can resolve a particular dimension associated with the size of the spot, such as width. This invention does not require that the spot be of a particular shape, such as round, square, or rectangular, as long as the detector array is oriented to resolve at least one dimension of the spot that is proportional to sample volume. Assuming the assay pad and the method by which the blood is delivered to the pad has been optimized to reduce the variability in spot development, the spot size will be proportional to the volume of blood sample.

The imaging system can resolve the spot size by identifying how many pixels or detector elements have detected a color change. Although the color change associated with the chemical reaction between analyte and enzyme may not be completed or reached equilibrium, the quantification of the number of pixels that have detected a predetermined threshold change in color will be proportional to the spot size. Thus, a real-time assessment of the spot size and thus volume can be computed.

Accordingly, the effect on glucose concentration calculations associated with various sample volumes may be empirically determined, and a lookup table, equation, or calculation incorporated in a memory device which may then be used to select an appropriate predetermined calibration factor to provide a more accurate reading of the analyte concentration for a particular sample volume. Thus, an appropriate calibration factor based on the actual sample volume may be applied to an algorithm used to calculate glucose concentration.

As an example of the above, if the glucose calibration curve is of the form:

R=m×[Glucose Concentration]+b; where R=the as-measured reflected light signal, and m and b are empirically determined constants. A corrected signal $R_c$, could be derived from a look-up table of correction factors, $F_v$, as a function of sample volume:

$$R_c = F_v \times R$$

This corrected signal would then be substituted into the above equation to calculate the volume-adjusted glucose concentration.

Various alternatives and modifications to the above-described embodiment related to detector array data analysis to determine sample size are possible, for example, such alternatives and modifications include one or more of: computing the number of pixels that have detected a change in color above a prescribed constant threshold at a particular point in time during the enzymatic reaction; computing the number of pixels that have detected a change in color above a prescribed constant threshold at multiple points in time during the enzymatic reaction; computing the number of pixels that have detected a change in color above a prescribed constant threshold at a time in which the enzymatic reaction is complete; computing the number of pixels that have detected a change in color above a variable threshold across the array; using above strategies to correlate output to actual sample volume at reagent pad; and using above strategies to predict sample volume to be delivered to assay pad after a predetermined amount of time.

Using the aforementioned detector array to detect the volume of the sample, the volume information can be used as feedback information, and utilized in devices such as an integrated meter. The definition of an integrated device or meter in this context includes one which includes the functions of acquiring a sample of body fluid or blood from the skin, transporting the body fluid or blood from the skin to a quantification area or assay pad, and quantifying the analyte (e.g.—glucose) in the sample via a photometric method.

In this embodiment, a catalyst such as vacuum, heat, pressure, vibration or similar action is preferably applied to the sampling site to facilitate the acquisition of sufficient sample volume of blood. Catalysts such as these can be effective in expressing sufficiently large volumes of blood even from alternative body sites that are less perfused than the fingertips. To ensure that the catalyst is applied with sufficient magnitude and duration, this invention provides a construction and method to control the catalyst such that it operates for exactly as long as necessary. By quantifying the sample volume delivered to the reagent pad in real-time, the detector array and associated on-board data processing within the integrated device can provide a feedback signal via a digital microprocessor controller or similar device which indicates either to increase, decrease, or keep constant the magnitude of the catalyst, as well as to either continue or stop the application of the catalyst. Those experienced in the art of controlling such catalyst mechanisms will appreciate that the control. signal may be either binary or analog and use this information accordingly to control a pump (for vacuum/pressure), a motor (for vibration), a heating element (for increasing skin temperature) or combinations thereof.

One such exemplary mode of operation is illustrated in FIG. 1. As illustrated therein, a suitable catalyst, such as a vacuum created by a suitable mechanism or pump is initiated. Shortly thereafter the signals from the detector array are analyzed and the sample volume estimated. This volume is compared with a target sample volume. If the volume is sufficient, the catalyst is turned off. If the volume is insufficient, the reading and calculating processes are repeated until such time as the target sample volume is reached. Once the target sample volume is reached, the analyte concentration determination may continue.

Various alternatives and modifications to the above-described embodiment related to detector array data analysis to provide feedback are possible. For example, such alternatives and modifications may include one or more of: providing a feedback signal corresponding to actual sample volume received at the assay pad; providing a feedback signal corresponding to predicted volume anticipated to be delivered to assay pad; providing an analog feedback signal that is proportional to the volume received at the assay pad; providing a digital feedback signal that indicates either sufficient or insufficient quantity of sample volume received; providing feedback signal based on imaging of an alternative location within the meter that is not necessarily the reagent pad, but can also be imaged by the detector array to detect whether a specific threshold of blood will be delivered to the reagent pad; and providing feedback signal based on imaging of an alternative location outside of the meter (such as on the skin) that can also be imaged by the detector array to detect whether a specific threshold of blood will be delivered to the assay pad.

The discrete nature of the detection elements or pixels also allows for detection of flaws and to distinguish them from regions of the reaction spot that are developing an appropriate or more ideal photometric reaction, even if they are randomly distributed.

For example, a detector array is arranged to scan the reaction spot, optionally coupled with appropriate optical magnification. An ideal spot will produce little or no variation in signal response across the array. In the case of a non-ideal spot, the response of the pixels will vary spatially and temporally. A quantification algorithm which has one or more of the following features could correct and/or ignore the reaction spot flaw(s) and have the potential to provide a more accurate measurement of the analyte concentration: identification and inclusion of data only from pixels which correspond to the appropriate and expected color (e.g., screen for data corresponding to various shades of blue only); identification and exclusion of data from pixels which do not correspond to the appropriate and expected color (e.g., screen out data corresponding to shades of red); inclusion/exclusion of pixel information which does not change at a rate with respect to time expected for the appropriate color (e.g., rate of change of blue is not the same as that of non-blue pixels); and inclusion/exclusion of pixel information which does not change at a rate with respect to time after a specific elapsed time or during a specific time window expected for the appropriate color (e.g., blue pixels change from time t1 to t2 by x %, whereas non-blue pixels do not change by x % between time t1 through t2).

Combinations of the above strategies or similar ones may allow the algorithm to successfully correct for non-ideal spots. It may even be the case that a relatively small percentage of the spot area actually is ideal, yet if the detector array can image this area, even 1 pixel could be sufficient to provide an accurate reading of the analyte.

Figure 2:
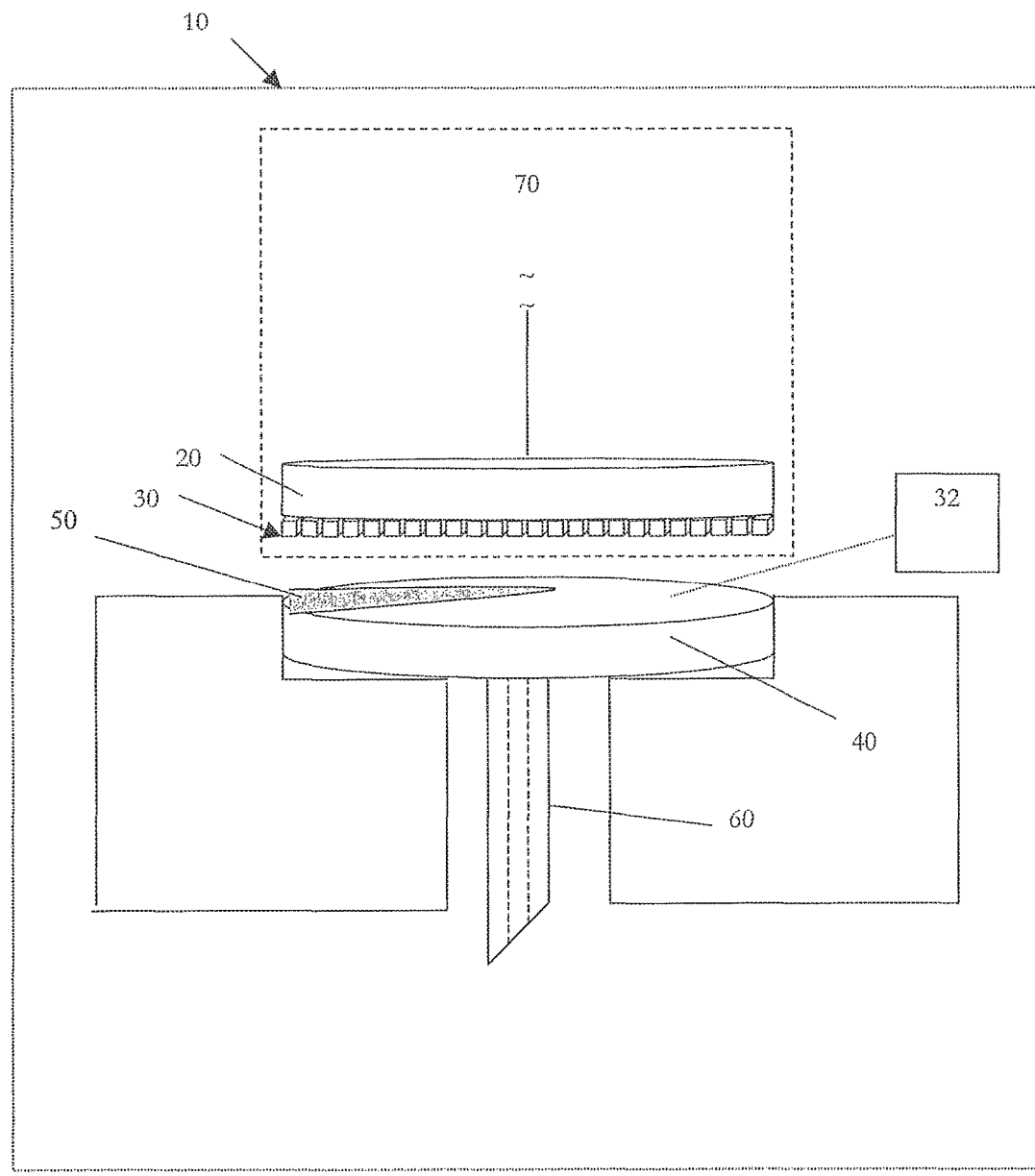
FIG. 2 is a schematic illustration of an arrangement formed according to the principles of the present invention.
Figure 3:
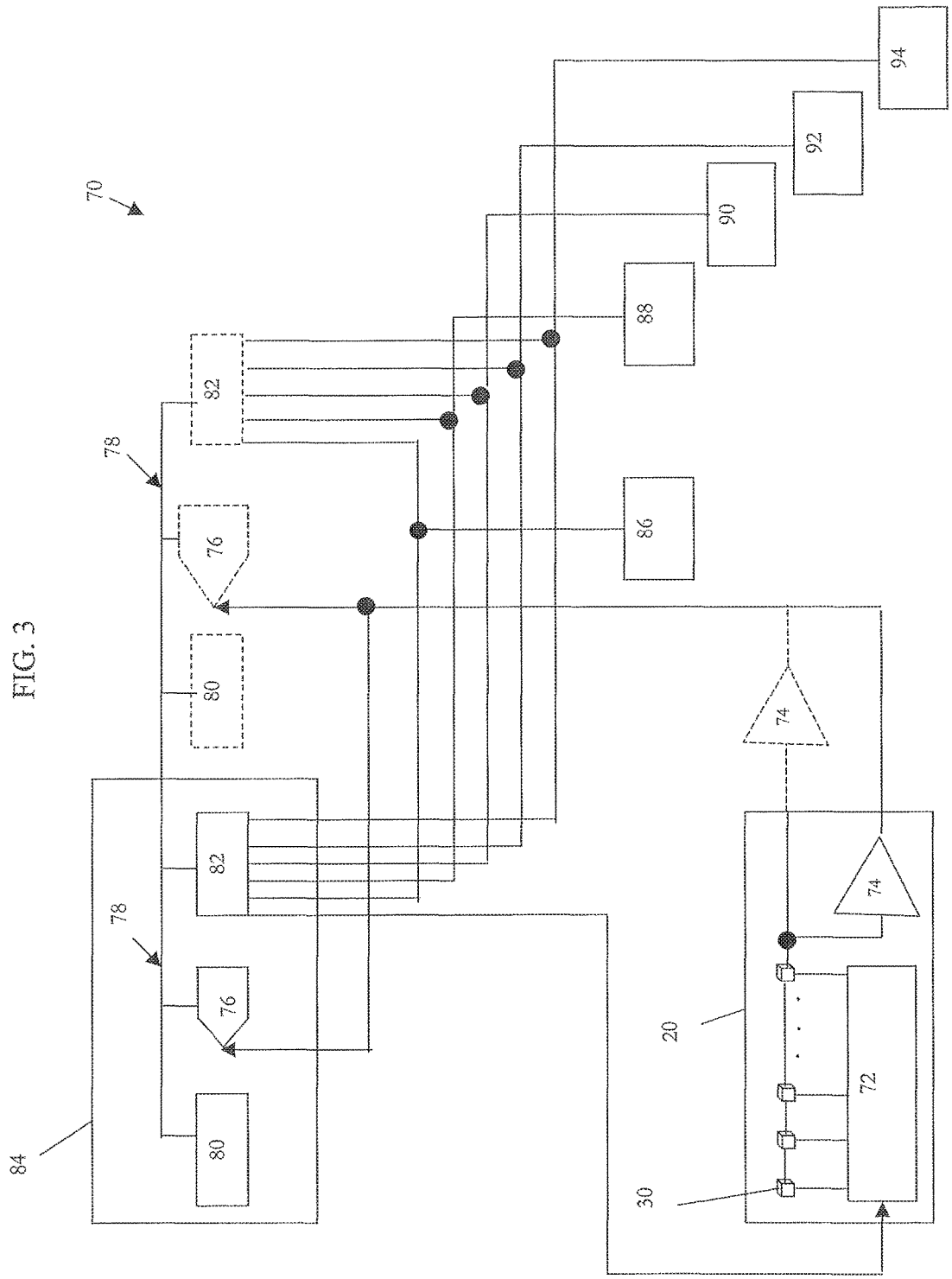
FIG. 3 is a schematic diagram of a portion of the arrangement of FIG. 2.

FIGS. 2-3 are schematic illustrations of at least some of the aspects of arrangements, devices and methods of the present invention. As illustrated therein, an arrangement 10, such as an integrated device or meter may include a detector array 20, which can be provided in the form of a linear array of individual detection elements 30. Each detection element 30 is capable of producing a signal. The detection elements 30 may comprise one or more CMOS-based detection elements or pixels. The linear array 20 is generally in optical registry with an assay pad 40. The relative vertical position of the assay pad and detector array 20 may, of course, differ from the illustrated embodiment. In addition, the assay pad 40 and the detector array 20 may have a geometry that differs from that of the illustrated embodiment. The detector array 20 may be larger than the assay pad 40.

The assay pad 40 preferably contains at least one reagent. A mechanism may be provided to transport a sample of body fluid, such as blood, to the assay pad 40. According to the illustrated embodiment, a hollow member 60, such as a needle, having one end in fluid communication with the assay pad may provide a mechanism for transport. As a sample of body fluid is applied to the assay pad 40, a reaction between the reagent and the analyte of interest (e.g., glucose) results in a color change on a surface of the assay pad 40 forming a reaction spot 50 in optical registry with the array of detector elements 30. The detector array 20 corresponds in location to the spot 50 produces a signal in response to the color change that is indicative of the presence of the analyte of interest. The signal can be used to estimate the volume of the sample applied to the reagent pad, monitor the kinetics of the reaction between the reagent and the analyte, and ascertain irregularities in the reaction spot 50, as described above. This information can then be used to correct the output (e.g., concentration of analyte present in the sample) of the device to account for the hematocrit level, volume of sample presented to the assay pad 40, and/or irregularities in the reaction spot 50. The above-described arrangement 10 of features may all be contained or integrated within a single device or meter.

Alternatively, one or a combination of any of the above-described features may be incorporated into such a device.

The detector array 20 forms part of an arrangement 70 present in the device 10 for carrying out the various operations described herein. As best illustrated in FIG. 3, the detector 20 may contain a plurality of detector elements in signal communication with a device 72 having timing and control logic. The timing and control logic may include internal as well external control signals. These signals typically include clock and frame start signals. External timing and control signals may be generated by a microprocessor/microcontroller or other external circuitry. The detector array 20 may have analog signal output. Alternatively, the detector 20 may have a digital data interface.

As illustrated, the detector may comprise an internal signal amplifier 74. Alternatively, the signal amplifier 74 may be external, as indicated by the amplifier 74 shown in broken line. According to another alternative, the amplifier 74 may be entirely omitted. According to yet another alternative, both an internal and external amplifiers 74 may be provided.

The signal from the detector 20 is outputted to an analog/digital converter 76 (where no digital data interface is provided by the detector). The converter 76 is connected to a bus 78, along with a memory 80 and an input/output device 82. The memory 80 may comprise one or more of RAM, ROM or EEPROM, as well as other conventional memory devices. Whatever its form, the memory 80 preferably contains at least one value indicative of hematocrit level, sample volume or reagent spot imperfections. In this regard the memory may contain one or more of the algorithms and look-up tables described herein.

The converter 76, the bus 78, the memory 80 and input/output device 82 may be components of a microprocessor/microcontroller 84. According to an alternative embodiment, the converter 76, memory 80 and input/output device 82 are external to the microprocessor/microcontroller 84.

The input/output device 82 is in signal communication with various output devices 86, 88, 90, 92, and can provide control signals thereto. These output devices may include a device providing a catalyst to facilitate sample acquisition, as described herein. For example, these devices may include one or more of a vacuum pump, an actuation trigger device, a light source, a heat source, a vibration motor, or combinations of any of the foregoing. Regardless of the form of these devices, they are configured and arranged such that they are in signal communication with input/output device 82 so as to be responsive to the control signals. These control signals may be based on sample volume calculations made with the assistance of the detector array, as described herein.

An integrated device formed according to the principles of the present invention may have a number of suitable configurations. According to certain embodiments the device is configured to perform testing by acquiring a sample of blood from the user, transfer the sample to an analysis site, and determine the concentration of a target analyte contained in the sample. These operations are all performed with little or no user input. For example, these operations may commence automatically according to a specified or predetermined schedule. Alternatively, these operations may commence at the command of the user via, for example, pressing a start button on the device.

The device may include disposable and reusable portions. The disposable portion may include at least one skin piercing element/transport member and analysis site (which may include an assay pad). The disposable portion may provide the capability to perform a single test. After testing is complete, the disposable portion is discarded and replaced with a new disposable portion before performing another test. Alternatively, the disposable portion includes a plurality of skin piercing elements/transport members and analysis sites. Such disposable units permit a plurality of tests to be performed before it is necessary to discard and replace the disposable unit. The device may be either wearable or handheld, or both.

Figure 4:
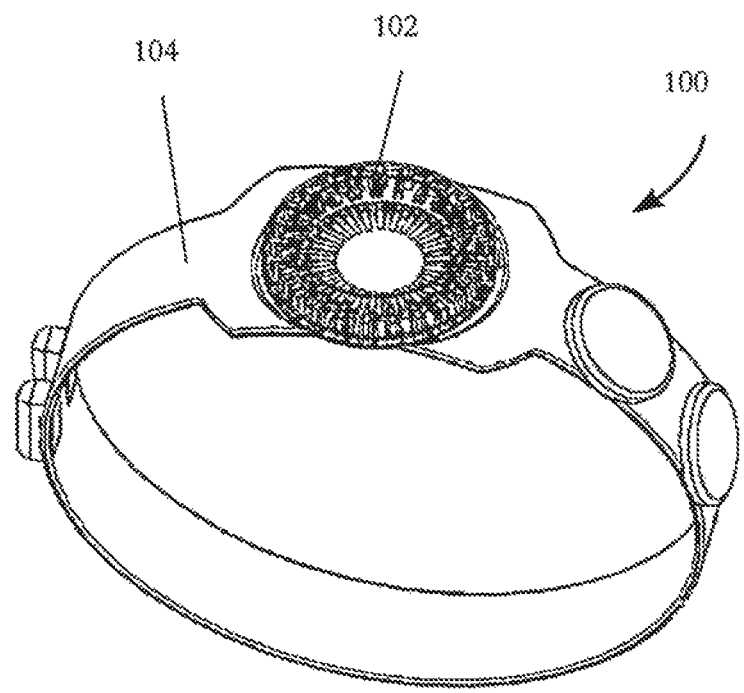
FIG. 4 is a perspective view of a device formed according to an embodiment of the present invention.
Figure 5:
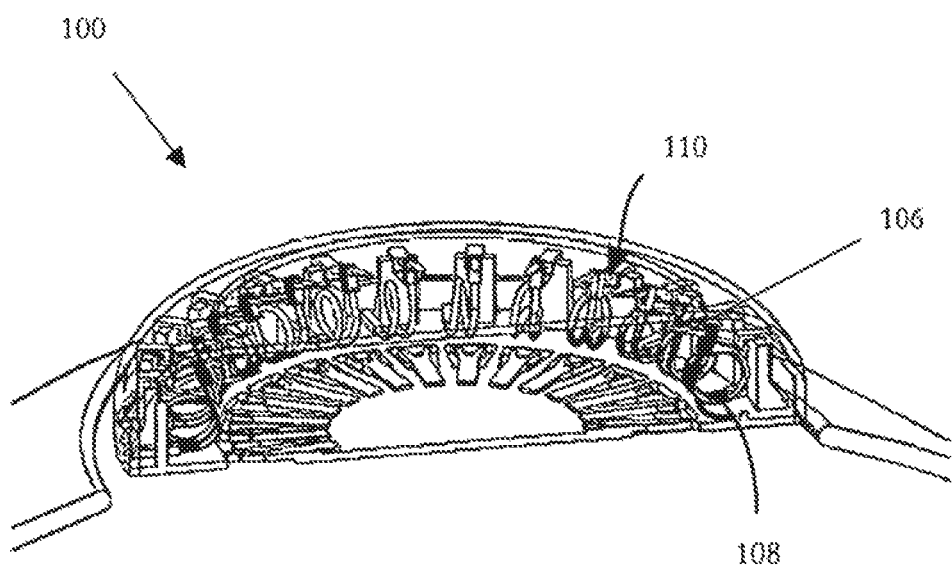
FIG. 5 is a partial cutaway view of FIG. 4.

A non-limiting exemplary integrated device 100 is illustrated in FIGS. 4-5. As illustrated therein the device 100 generally comprises a functional portion 102, and an optional attachment means or band 104. Thus according to the present invention, the integrated device 100 may be wearable. In addition, or alternatively, the integrated device may be operable as a hand-held device. For example, according to the illustrated embodiment, the band 104 can be separated and/or otherwise removed from the user, and the device 100 stored in a suitable case or in the user's pocket. The band can then be grasped and used to hold the device against the skin to perform a testing operation.

The device 100 preferably includes at least one arrangement for performing a measurement of the concentration of an analyte contained in a sample of blood. According to the illustrated embodiment, the device 100 comprises at least one skin-piercing element, at least one actuation member, such as a torsional spring element as described in further detail herein, and at least one analysis site 110, which may contain an assay pad. The at least one arrangement may form part of a disposable portion or unit. According to one embodiment, the disposable unit allows for at least one measurement of the concentration of an analyte contained in a sample of blood prior to being discarded and replaced. According to a further embodiment, the disposable unit allows for a plurality of measurements of the concentration of an analyte contained in a sample of blood prior to being discarded and replaced.

According to certain alternative embodiments, the device may additionally contain one or more of the features disclosed in U.S. Pat. No. 6,540,975, U.S. Patent Application Publications 2003/0153900, 2004/0191119, and published PCT Applications WO 04/085995 and WO 04/0191693, the entire contents of which are incorporated herein by reference.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The abstract and the title are not to be construed as limiting the scope of the present invention, as their purpose is to enable the appropriate authorities, as well as the general public, to quickly determine the general nature of the invention. Unless the term "means" is expressly used, none of the features or elements recited herein should be construed as means-plus-function limitations pursuant to 35 U.S.C. § 112, ¶6.

We claim:

1. An arrangement for measuring a concentration of an analyte contained in a sample of body fluid, the arrangement comprising:

an assay pad containing a single chemical reagent, wherein the chemical reagent produces a detectable signal in the form of a color change at a reaction spot formed upon reaction with the analyte, and wherein the concentration of the analyte is measured at the reaction spot;
a light source;
a detector array; and
a processor configured to:
   derive a hematocrit level value from the color change at the reaction spot; and
   calculate a hematocrit-adjusted analyte concentration using the hematocrit level value.

2. The arrangement of claim 1, wherein the analyte comprises glucose and the body fluid comprises blood.

3. The arrangement of claim 1, wherein the detector array is a linear array.

4. The arrangement of claim 1, wherein the detector array comprises at least one of a linear array, a polar array, and an area array.

5. The arrangement of claim 1, wherein the detector array comprises a plurality of detector elements, the detector elements comprising CMOS, CCD, photodiode, infrared, fluorescent, or ultraviolet elements.

6. The arrangement of claim 1, further comprising at least one body fluid sampling catalyst device.

7. The arrangement of claim 6, wherein the at least one catalyst device comprises at least one of a vacuum pump, a vibration motor, and a heating element.

8. The arrangement of claim 7, wherein the at least one catalyst device is configured to be responsive to control signals, the control signals based on sample volume calculations.

9. The arrangement of claim 5, wherein at least a portion of the plurality of detector elements are not in optical registry with the reaction spot and are configured to analyze one or more of a control solution having a known concentration of analyte introduced onto an area of the assay pad that is different from the area of the reaction spot, a standard color producing a known signal, and calibration information specific to the lot of the assay pad.

10. The arrangement of claim 1 further comprising a memory, wherein the processor is further configured to look-up the hematocrit level value in a look-up table stored on the memory.

11. The arrangement of claim 1, further comprising a needle having a first end configured to pierce skin, and a second end in fluid communication with the assay pad.

12. An analyte monitoring device comprising the arrangement of claim 1, wherein the arrangement comprises a plurality of assay pads and a plurality of needles, thereby enabling the performance of a plurality of analyte concentration measurements.

13. The analyte monitoring device of claim 12, further comprising a band for attaching the device to a body of a user.

14. An integrated meter comprising:
   at least one piercing element;
   at least one actuation member; and
   the arrangement of claim 1.

15. An arrangement for measuring a concentration of an analyte contained in a sample of body fluid, the arrangement comprising:

an assay pad comprising a chemical reagent configured to produce a detectable color change in a reaction with the analyte, wherein the detectable color change is indicative of an analyte level;
a light source;
a detector array; and
a processor configured to:
   derive a calibration factor from the detectable color change of the same reaction, wherein the calibration factor is indicative of the level of hematocrit contained in the sample; and
   calculate the concentration of the analyte using the analyte level and the calibration factor.

16. The arrangement of claim 15, wherein the analyte comprises glucose and the body fluid comprises blood.

17. The arrangement of claim 15, wherein the detector array is a linear array.

18. The arrangement of claim 15, wherein the detector array comprises at least one of a linear array, a polar array, and an area array.

19. The arrangement of claim 15, wherein the detector array comprises a plurality of detector elements, the detector elements comprising CMOS, CCD, photodiode, infrared, fluorescent, or ultraviolet elements.

20. The arrangement of claim 15, further comprising at least one body fluid sampling catalyst device.

21. The arrangement of claim 20, wherein the at least one catalyst device comprises at least one of a vacuum pump, a vibration motor, and a heating element.

22. The arrangement of claim 21, wherein the at least one catalyst device is configured to be responsive to control signals, the control signals based on sample volume calculations.

23. The arrangement of claim 19, wherein at least a portion of the plurality of detector elements are not in optical registry with a reaction spot formed by the reaction and are configured to analyze one or more of a control solution having a known concentration of analyte introduced onto an area of the assay pad that is different from the area of the reaction spot, a standard color producing a known signal, and calibration information specific to the lot of the assay pad.

24. The arrangement of claim 15 further comprising a memory, wherein the processor is further configured to look-up the calibration factor in a look-up table stored on the memory.

25. The arrangement of claim 15, further comprising a needle having a first end configured to pierce skin, and a second end in fluid communication with the assay pad.

26. An analyte monitoring device comprising the arrangement of claim 15, wherein the arrangement comprises a plurality of assay pads and a plurality of needles, thereby enabling the performance of a plurality of analyte concentration measurements.

27. The analyte monitoring device of claim 26, further comprising a band for attaching the device to a body of a user.

28. An integrated meter comprising:
   at least one piercing element;
   at least one actuation member; and
   the arrangement of claim 15.

* * * * *